United States Patent [19]

Tamao et al.

[11] Patent Number: 5,789,609
[45] Date of Patent: Aug. 4, 1998

[54] OPTICALLY ACTIVE DIPHOSPHINE, TRANSITION METAL COMPLEX CONTAINING THE SAME, AND PROCESS FOR PRODUCING OPTICALLY ACTIVE COMPOUND USING THE COMPLEX

[75] Inventors: Kyoko Tamao, Kyoto; Koji Inagaki, Mie; Noboru Sayo, Kanagawa, all of Japan

[73] Assignee: Takasago International Corporation, Tokyo, Japan

[21] Appl. No.: 956,048

[22] Filed: Oct. 22, 1997

[30] Foreign Application Priority Data

Oct. 30, 1996 [JP] Japan ................... 8-303555

[51] Int. Cl.⁶ ................ C07F 15/00; C07F 9/02; C07C 261/00
[52] U.S. Cl. ................ 556/18; 556/21; 556/136; 560/160; 560/174; 560/243; 560/247; 560/19; 560/51; 568/13; 568/17
[58] Field of Search ................ 568/13, 17; 556/18, 556/21, 136; 560/160, 174, 19, 51, 243, 247

[56] References Cited

U.S. PATENT DOCUMENTS

| 4,879,008 | 11/1989 | Puckette | 204/72 |
| 4,904,808 | 2/1990 | Devon et al. | 556/21 |
| 5,026,886 | 6/1991 | Stavinoha et al. | 556/70 |
| 5,516,944 | 5/1996 | Broger et al. | 568/13 |
| 5,600,006 | 2/1997 | Regnat et al. | 568/16 |
| 5,631,393 | 5/1997 | Kohlpaintner et al. | 556/17 |
| 5,693,868 | 12/1997 | Sayo et al. | 568/8 |
| 5,696,296 | 12/1997 | Naumann et al. | 568/17 |

OTHER PUBLICATIONS

*J. Am. Chem. Soc.*, vol. 113, p. 1417 (1991).
*J. Org. Chem.*, vol. 54, p. 4738 (1989).
*J. Am. Chem. Soc.*, vol. 114, p. 8295 (1992).
*Tetrahedron: Asymmetry*, vol. 5, p. 325 (1994).
*J. Org. Chem.*, vol. 59, p. 3151 (1994).

*Primary Examiner*—Porfirio Nazario-Gonzalez
*Attorney, Agent, or Firm*—Sughrue, Mion, Zinn, Macpeak & Seas, PLLC

[57] ABSTRACT

Disclosed are an optically active diphosphine represented by formula:

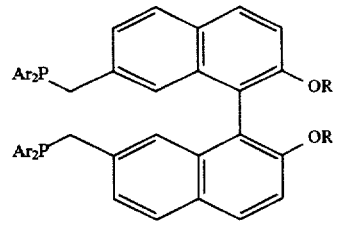

wherein R represents a lower alkyl group having 1 to 4 carbon atoms; Ar represents a phenyl group which may be substituted with a lower alkyl group having 1 to 4 carbon atoms and/or a lower alkoxy group having 1 to 4 carbon atoms, a transition metal complex containing the diphosphine as a ligand, and a process for producing an optically active δ-oxo-α-cyano ester using the transition metal complex as a catalyst.

4 Claims, No Drawings

5,789,609

1

OPTICALLY ACTIVE DIPHOSPHINE, TRANSITION METAL COMPLEX CONTAINING THE SAME, AND PROCESS FOR PRODUCING OPTICALLY ACTIVE COMPOUND USING THE COMPLEX

FIELD OF THE INVENTION

This invention relates to a novel optically active diphosphine. More particularly, it relates to an optically active diphosphine, a transition metal complex containing the same as a ligand which is useful as a catalyst for various asymmetric syntheses, and a process for producing an optically active compound making use of the complex catalyst.

BACKGROUND OF THE INVENTION

A great number of transition metal complexes have been used as a catalyst for organic synthesis reactions. In particular, noble metal complexes have enjoyed wide use for their stability and ease of handling in spite of expensiveness. Extensive study has been given to use of transition metal complexes, such as nobel metal complexes, as a catalyst in various syntheses, and we can find many reports on the transition metal complexes which have effected organic synthesis reactions, inclusive of asymmetric reactions, that had been regarded as impossible with conventional means.

Optically active ligands useful in asymmetric catalytic reactions include various types. 2,2'-Bis (diphenylphosphino)-1,1'-binaphthyl (hereinafter simply referred to as BINAP) is among the optically active ligands having the most excellent ability of recognizing asymmetry. Palladium catalysts having BINAP as a ligand exhibit very excellent catalytic activity and enantiomer selectivity in a Heck's reaction of olefins forming an asymmetric carbon-carbon bond, as reported in Ozawa et al., *J. Am. Chem. Soc.*, Vol. 113, p. 1417 (1991) and Shibazaki et al., *J. Org. Chem.*, Vol. 54, p. 4738 (1989).

However, the state-of-the-art transition metal complex catalysts are hardly effective in other carbon-carbon bond forming reactions, such as Michael's addition reaction. Recently Itoh et al. reported a ligand composed of two ferrocenyl groups called TRAP which has $C_2$ chirality and is trans-coordinated to a metal (*J. Am. Chem. Soc.*, Vol. 114, p. 8295 (1992)). According to the report, the ligand was found to exhibit excellent performance in Michael's addition reaction. However, this ligand is difficult to synthesize on an industrial scale because the reagent necessary for the synthesis is difficult to handle.

Takaya et al. reported synthesis of a ligand having a diphenylphosphino group at the 7,7'-positions of a binaphthyl skeleton (*Tetrahedron: Asymmetry*, Vol. 5, p. 325 (1994)), but there is no report on an asymmetric reaction utilizing this ligand.

SUMMARY OF THE INVENTION

An object of the present invention is to provide a diphosphine ligand as a catalyst for asymmetric synthesis reaction which, being different from the conventional BINAP derivatives, exhibits excellent performance in selectivity to a substrate, reaction conversion, catalytic activity, and optical purity.

Another object of the present invention is to provide a transition metal complex prepared from such a diphosphine ligand and a transition metal compound.

A further object of the present invention is to provide a process for producing an optically active δ-oxo-α-cyano ester by adding an α-cyano ester to a vinyl ketone compound in the presence of the transition metal complex.

The inventors of the present invention have devoted their study to a ligand having an ability of catalyzing asymmetric synthesis reactions and found as a result that a diphosphine compound having a diphenylphosphinomethyl group at the 7,7'-positions of a binaphthyl skeleton is extremely excellent as a ligand in asymmetric catalytic reactions. The present invention has been completed based on this finding.

The above object of the invention is accomplished by an optically active diphosphine represented by formula (1):

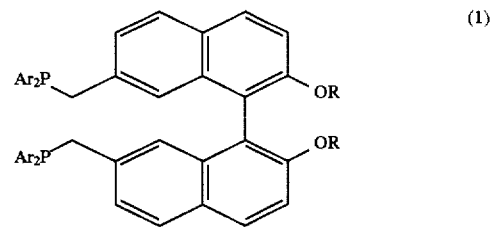

wherein R represents a lower alkyl group having 1 to 4 carbon atoms; Ar represents a phenyl group which may be substituted with a lower alkyl group having 1 to 4 carbon atoms and/or a lower alkoxy group having 1 to 4 carbon atoms.

DETAILED DESCRIPTION OF THE INVENTION

In formula (1), the lower alkyl group as represented by R includes methyl, ethyl, propyl, isopropyl, n-butyl, and t-butyl groups. The substituted or unsubstituted phenyl group as represented by Ar includes phenyl, 4-tolyl, 4-anisyl, and 3,5-xylyl groups.

The phosphine (1) takes an optically active form and a racemic form, both of which are included under the scope of the present invention.

The diphosphine ligand (1), for example, the compound in which R is a methyl group and Ar is a phenyl group can be prepared in accordance with the following reaction scheme. In the formulae shown below, t-Bu represents a t-butyl group; Me, a methyl group; Et, an ethyl group; THF, tetrahydrofuran; Tf, a trifluoromethanesulfonyl group; Ac, an acetyl group; DPPP, diphenylphosphinopropane; i-Pr, an isopropyl group; DMSO, dimethyl sulfoxide; and Ph, a phenyl group (hereinafter the same).

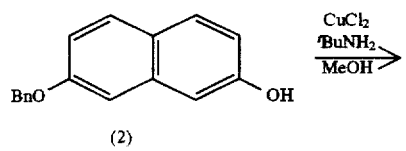

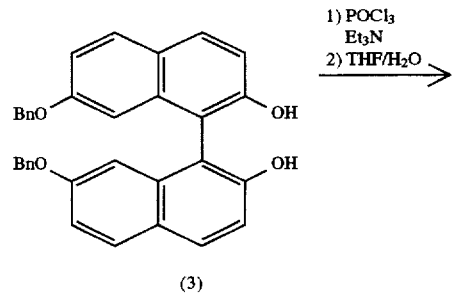

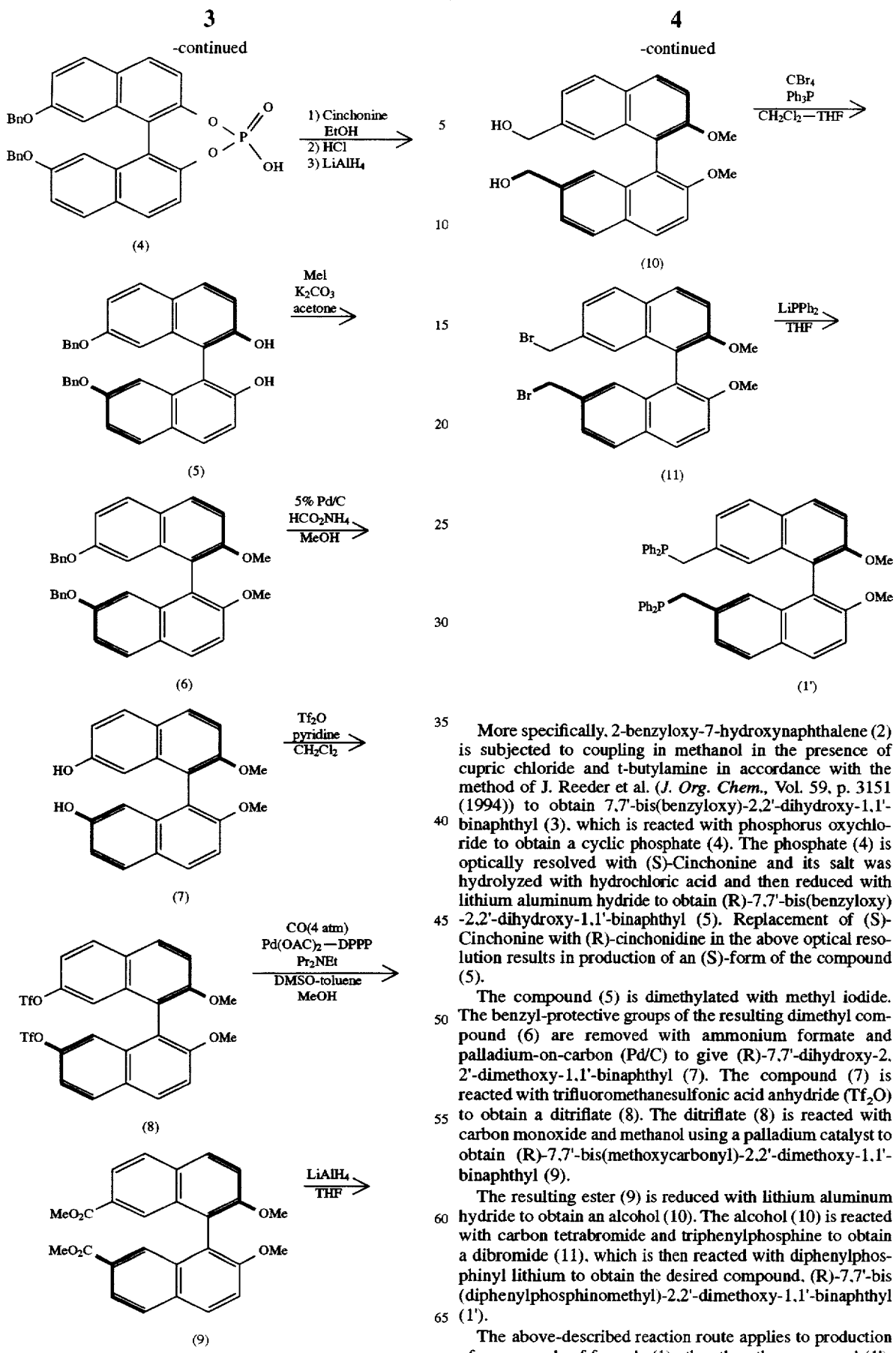

More specifically, 2-benzyloxy-7-hydroxynaphthalene (2) is subjected to coupling in methanol in the presence of cupric chloride and t-butylamine in accordance with the method of J. Reeder et al. (*J. Org. Chem.*, Vol. 59, p. 3151 (1994)) to obtain 7,7'-bis(benzyloxy)-2,2'-dihydroxy-1,1'-binaphthyl (3), which is reacted with phosphorus oxychloride to obtain a cyclic phosphate (4). The phosphate (4) is optically resolved with (S)-Cinchonine and its salt was hydrolyzed with hydrochloric acid and then reduced with lithium aluminum hydride to obtain (R)-7,7'-bis(benzyloxy)-2,2'-dihydroxy-1,1'-binaphthyl (5). Replacement of (S)-Cinchonine with (R)-cinchonidine in the above optical resolution results in production of an (S)-form of the compound (5).

The compound (5) is dimethylated with methyl iodide. The benzyl-protective groups of the resulting dimethyl compound (6) are removed with ammonium formate and palladium-on-carbon (Pd/C) to give (R)-7,7'-dihydroxy-2,2'-dimethoxy-1,1'-binaphthyl (7). The compound (7) is reacted with trifluoromethanesulfonic acid anhydride ($Tf_2O$) to obtain a ditriflate (8). The ditriflate (8) is reacted with carbon monoxide and methanol using a palladium catalyst to obtain (R)-7,7'-bis(methoxycarbonyl)-2,2'-dimethoxy-1,1'-binaphthyl (9).

The resulting ester (9) is reduced with lithium aluminum hydride to obtain an alcohol (10). The alcohol (10) is reacted with carbon tetrabromide and triphenylphosphine to obtain a dibromide (11), which is then reacted with diphenylphosphinyl lithium to obtain the desired compound, (R)-7,7'-bis(diphenylphosphinomethyl)-2,2'-dimethoxy-1,1'-binaphthyl (1').

The above-described reaction route applies to production of compounds of formula (1) other than the compound (1').

The compound (1) of the present invention serves as a ligand forming a complex with a transition metal. Metals forming the complex include rhodium, palladium, ruthenium, iridium, and nickel. Preferred transition metals are rhodium, palladium, ruthenium and iridium. Examples of the transition metal complexes obtained by using the compound (1) are shown below. In the following formulae, cod stands for 1,5-cyclooctadiene; nbd for norbornadiene; acac for acetylacetonato; and L represents (R)-7,7'-bis (diphenylphosphinomethyl)-2,2'-dimethoxy-1,1'-binaphthyl as a typical example of the compound (1).

Rhodium Complexes:

Rhodium complexes can be prepared in accordance with the process described in The Chemical Society of Japan (ed.), *Jikken Kagaku Koza* (4th Ed.), Vol. 18, "Yuki Kinzoku Sakutai", pp. 339–344, Maruzen (1991). For example, the compound (1) is reacted with bis(cycloocta-1,5-diene) rhodium (I) tetrafluoroborate. Specific examples of the thus prepared rhodium complexes are listed below.

Rh(CO)(acac)(L)
[Rh(cod)(L)]ClO$_4$
[Rh(cod)(L)]PF$_6$
[Rh(cod)(L)]BF$_4$
[Rh(nbd)(L)]ClO$_4$
[Rh(nbd)(L)]PF$_6$
[Rh(nbd)(L)]BF$_4$
Rh(cod)(L)Cl
Rh(nbd)(L)Cl
Rh(cod)(L)Br
Rh(nbd)(L)Br Palladium Complexes:

Palladium complexes can be prepared by reacting L with, for example, π-allylpalladium chloride in accordance with the process described in Y. Uozumi and T. Hayashi, *J. Am. Chem. Soc.*, Vol. 113, p. 9887 (1991). Examples of the resulting palladium complexes are shown below:

PdCl$_2$(L)
(π-allyl)Pd(L)
[Pd(L)]ClO$_4$
[Pd(L)]PF$_6$
[Pd(L)]BF$_4$

Ruthenium Complexes:

Ruthenium complexes can be prepared by reacting L with, for example, [Ru(p-cymene)I$_2$]$_2$ by heating while stirring in methylene chloride and ethanol in accordance with the process of Mashima et al. (K. Mashima et al., *J. Chem. Soc., Chem. Commun.*, p. 1208 (1989)). Examples of the resulting ruthenium complexes are shown below.

[RuCl(benzene)(L)]Cl
[RuBr(benzene)(L)]Br
[RuI(benzene)(L)]I
[RuCl(p-cymene)(L)]Cl
[RuBr(p-cymene)(L)]Br
[RuI(p-cymene)(L)]I
[RuCl(mesitylene)(L)]Cl
[RuBr(mesitylene)(L)]Br
[RuI(mesitylene)(L)]I
[RuCl(hexamethylbenzene)(L)]Cl
[RuBr(hexamethylbenzene)(L)]Br
[RuI(hexamethylbenzene)(L)]I Iridium Complexes:

Iridium complexes can be prepared by reacting L with, for example, [Ir(cod) (CH$_3$CN)$_2$]BF$_4$ in tetrahydrofuran while stirring in accordance with the process of Mashima et al. (K. Mashima et al., *J. Organomet. Chem.*, Vol. 428, p. 213 (1992)). Examples of the resulting iridium complexes are shown below.

[Ir(cod)(L)]ClO$_4$
[Ir(cod)(L)]PF$_6$
[Ir(cod)(L)]BF$_4$
[Ir(nbd)(L)]ClO$_4$
[Ir(nbd)(L)]PF$_6$
[Ir(nbd)(L)]BF$_4$
Ir(cod)(L)Cl
Ir(nbd)(L)Cl
Ir(cod)(L)Br
Ir(nbd)(L)Br The transition metal complex obtained from the diphosphine (1) and a transition metal compound can be made use of as a catalyst for asymmetric syntheses. For example, it is useful as a catalyst for addition reaction of an α-cyano ester (A) to a vinyl ketone compound (B) to prepare an optically active δ-oxo-α-cyano ester (C) (Michael's addition reaction) as illustrated below.

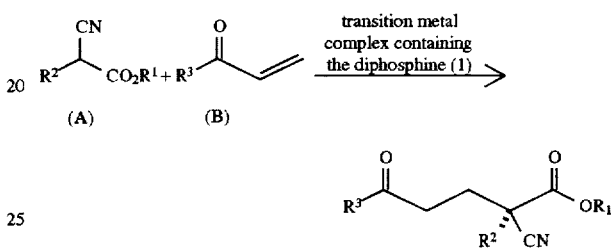

wherein R$^1$ represents an alkyl group having 1 to 8 carbon atoms; R$^2$ represents a lower alkyl group having 1 to 4 carbon atoms; and R$^3$ represents a lower alkyl group having 1 to 4 carbon atoms or a substituted or unsubstituted phenyl group. Specific examples of the substituents for the substituted phenyl group include a halogen atom, a lower alkyl group and a halogenated lower alkyl group.

That is, an optically active δ-oxo-α-cyano ester having a desired absolute configuration is synthesized by using, as a catalyst, a transition metal complex containing the diphosphine (1) of selected isomer, either an (R)-isomer or an (S)-isomer, as a ligand.

In the α-cyano ester (A), R$^1$ includes methyl, ethyl, propyl, isopropyl, n-butyl, t-butyl, and diisopropylmethyl groups; and R$^2$ includes methyl, ethyl, propyl, isopropyl, n-butyl, and t-butyl groups. In the vinyl ketone compound (B), R$^3$ includes methyl, ethyl, propyl, isopropyl, n-butyl, t-butyl, phenyl, 2-, 3- or 4-anisyl, 2-, 3- or 4-chlorophenyl, 2-, 3- or 4-fluorophenyl, 2-, 3- or 4-trifluoromethylphenyl, and 2-, 3- or 4-tolyl groups.

Solvents which can be used in the reaction include methanol, ethanol, isopropyl alcohol, benzene, toluene, ethyl acetate, tetrahydrofuran, methylene chloride, 1,2-dichloroethane, and acetone.

The catalyst is used in an amount of about 0.01 to 10 mol %, preferably about 0.05 to 5 mol %, based on the reaction substrate.

While the reaction temperature and time are subject to variation depending on the amount of the reactants used, the reaction is usually carried out at about 10° to 100° C., preferably about 20° to 50° C., for about 10 to 100 hours.

The diphosphine according to the present invention is an excellent ligand for asymmetric syntheses. A transition metal complex formed of ruthenium, rhodium or a like transition metal and the diphosphine ligand exhibits excellent catalytic performance in selectivity, conversion, catalytic activity, and the like in asymmetric syntheses, such as an asymmetric Michael's addition reaction.

The present invention will now be illustrated in greater detail with reference to Examples, but it should be understood that the invention is not construed as being limited thereto.

Physical properties of the compounds produced in Examples were measured with the following equipment.
NMR Spectrometer:

$^1$H-NMR: JMN-EX-270 (270 MHz), manufactured by JEOL Ltd.

$^1$P-NMR: JMN-EX-270 (109 MHz), manufactured by JEOL Ltd.

Polarimeter: DIP-360, manufactured by JASCO, Inc.

Gas chromatograph: QC-15A, manufactured by Shimadzu Corp.

Mass Spectrometer: QP-1000, manufactured by Shimadzu Corp.

REFERENCE EXAMPLE 1

Synthesis of 7,7'-Bis(benzyloxy)-2,2'-dihydroxy-1,1'-binaphthyl

To 23.6 g (0.094 mol) of 2-benzyloxy-7-hydroxynaphthalene and 25.6 g (0.19 mol) of cupric chloride was added 600 ml of methanol, and 56.32 g (0.77 mol) of t-butylamine and 200 ml of methanol were added thereto dropwise over a period of 1.5 hours, followed by stirring for 20 hours. The reaction mixture was cooled with an ice bath, and 200 ml of a 6N hydrochloric acid aqueous solution was added thereto dropwise. The reaction mixture was concentrated with an evaporator. Ethyl acetate was added to the residue, followed by liquid-liquid separation. The organic layer was washed with a saturated sodium chloride aqueous solution, and the solvent was removed by evaporation. The residue was recrystallized from toluene-cyclohexane to yield 20 g (85%) of the title compound.

$^1$H-NMR (CDCl$_3$) δ: 4.69 and 4.83 (d, J=11.8 Hz, 4H), 4.99 (s, 2H), 6.48 (d, J=2.4 Hz, 2H), 7.10 (dd, J=9.0 and 2.4 Hz, 2H), 7.15–7.25 (m, 12H), 7.80 (d, J=9.0 Hz, 2H), 7.89 (d, J=9.0 Hz, 2H)

REFERENCE EXAMPLE 2

Optical Resolution of 7,7'-Bis(benzyloxy)-2,2'-dihydroxy-1,1'-binaphthyl (a) To a solution of 33.7 g (67.7 mmol) of 7,7'-bis(benzyloxy)-2,2'-dihydroxy-1,1'-binaphthyl in 100 ml of methylene chloride were added 16 ml (171.7 mmol) of phosphorus oxychloride and then 25 ml (179.2 mmol) of triethylamine. The reaction mixture was stirred for 1 hour at 20° C. (following initial heat generation). The reaction mixture was poured into 200 ml of ice-water for liquid-liquid separation. The organic layer was washed with two 100 ml portions of water, and the solvent was removed off with an evaporator. To the residue was added 300 ml of a mixture of tetrahydrofuran (THF) and water, followed by refluxing for 2 hours. The reaction mixture was extracted with three 100 ml portions of ethyl acetate and washed with a saturated sodium chloride aqueous solution. The solvent was removed by evaporation to give 36.7 g (97%) of 7,7'-bis(benzyloxy-1,1'-binaphthyl)-2,2'-diyl hydrogenphosphate.

(b) To 300 ml of ethanol were added 27.1 g (48.4 mmol) of 7,7'-bis(benzyloxy-1,1'-binaphthyl)-2,2'-diyl hydrogenphosphate and 14.3 g (48.6 mmol) of Cinchonine, and the mixture was refluxed to dissolve, followed by gradual cooling. The precipitated crystals (16.5 g) were collected by filtration. The filtrate was concentrated to recover 3.7 g of the crystals. Recrystallization of the combined crystals from ethanol/water (4/1 by volume) gave 12.1 g (59%) of a Cinchonine salt.

(c) In 200 ml of chloroform was dissolved 12 g (14 mmol) of the resulting Cinchonine salt and extracted with three 75 ml portions of a 6N hydrochloric acid aqueous solution. The organic layer was washed with water, and the solvent was evaporated to afford 7.9 g (100%) of (−)-7,7'-bis(benzyloxy)-1,1'-binaphthyl-2,2'-diyl hydrogenphosphate.

(d) In 150 ml of THF was dissolved 6.0 g (10.7 mmol) of (−)-7,7'-bis(benzyloxy-1,1'-binaphthyl)-2,2'-diyl hydrogenphosphate, and 2 g (50 mmol) of lithium aluminum hydride was added to the solution. The reaction mixture was refluxed for 2 hours, followed by cooling on an ice bath. Water was slowly added thereto dropwise, and the reaction mixture was extracted with ethyl acetate. The extract was washed with a saturated sodium chloride aqueous solution, and the solvent was evaporated to give 5.05 g (95%) of (R)-(−)-7,7'-bis(benzyloxy)-2,2'-dihydroxy-1,1'-binaphthyl.

EXAMPLE 1

Synthesis of (R)-(−)-7,7'-Bis(benzyloxy)-2,2'-dimethoxy-1,1'-binaphthyl

Acetone (80 ml) was added to a mixture of 7.37 g (14.6 mmol) of dihydroxy-1,1'-binaphthyl and 7.37 g (53.3 mmol) of potassium carbonate, and 2.8 ml (45.0 mmol) of methyl iodide was added thereto, followed by stirring at room temperature for 60 hours. The reaction mixture was filtered, and the filtrate was concentrated. Recrystallization of the residue from isopropyl alcohol yielded 5.89 g (76%) of the title compound.

Melting point: 126.5°–127° C. $[\alpha]_D^{23}$: −132° (c=1.28, CHCl$_3$).

$^1$H-NMR (270 MHz, CDCl$_3$)δ: 3.66 (s, 6H), 4.70 (s, 4H), 6.43 (d, J=2.3 Hz, 2H), 7.06 (dd, J=8.9, 2.6 Hz, 2H), 7.10–7.14 (m, 4H), 7.17–7.21 (m, 4H), 7.77 (d, J=9.2 Hz, 2H), 7.88 (d, J=8.9 Hz, 2H)

EXAMPLE 2

Synthesis of (R)-(−)-7,7'-Dihydroxy-2,2'-dimethoxy-1,1'-binaphthyl

Methanol (140 ml) was added to a mixture of 5.89 g (11.2 mmol) of (R)-(−)-7,7'-bis(benzyloxy)-2,2'-dimethoxy-1,1'-binaphthyl, 11.9 g (5.59 mmol) of 5% Pd/C, and 7.11 g (113 mmol) of ammonium formate, and the mixture was refluxed for 63 hours. After cooling to room temperature, the reaction mixture was filtered using Celite. The filtrate was concentrated. Diethyl ether was added to the concentrate, and the mixture was washed with water. The solvent was evaporated to give 3.33 g (86%) of the title compound.

Melting point: 207°–209° C. $[\alpha]_D^{23}$: −119° (c=1.07, EtOH).

$^1$H-NMR (270 MHz, CDCl$_3$) δ: 3.75 (s, 6H), 4.81 (s, 2H), 6.36 (d, J=2.3 Hz, 2H), 6.93 (dd, J=8.9, 2.3 Hz, 2H), 7.27 (d, J=8.9 Hz, 2H), 7.76 (d, J=8.9 Hz, 2H), 7.87 (d, J=8.9 Hz, 2H)

EXAMPLE 3

Synthesis of (R)-(−)-7,7'-Bis(trifluoromethanesulfonyloxy)-2,2'-dimethoxy-1,1'-binaphthyl In 80 ml of methylene chloride were dissolved 4.48 g (12.9 mmol) of (R)-(−)-7,7'-dihydroxy-2,2'-dimethoxy-1,1'-binaphthyl and 3.2 ml (39.6 mmol) of pyridine. The solution was cooled on an ice bath, and 5.3 ml (31.5 mmol) of trifluoromethanesulfonic acid anhydride was added thereto, followed by stirring at room temperature for 4 hours. The reaction mixture was concentrated, and ethyl acetate was added to the residue. The mixture was washed successively with a 1N hydrochloric acid aqueous solution, a saturated sodium hydrogencarbonate aqueous solution, and a saturated sodium chloride aqueous solution. The solvent was evaporated to give 7.8 g (100%) of the title compound.

Melting point: 139°–141° C. $[\alpha]_D^{22}$: –61° (c=1.17, $CHCl_3$).

$^1$H-NMR (270 MHz, $CDCl_3$) δ: 3.79 (s, 6H), 4.81 (s, 2H), 6.97 (d, J=2.6 Hz, 2H), 7.22 (dd, J=8.9, 2.6 Hz, 2H), 7.53 (d, J=9.2 Hz, 2H), 7.96 (d, J=9.2 Hz, 2H), 8.06 (d, J=8.9 Hz, 2H).

EXAMPLE 4

Synthesis of (R)-(–)-Dimethyl 2,2'-dimethoxy-1,1'-binaphthalene-7,7'-dicarboxylate In a 100 ml autoclave were put 3.0 g (4.92 mmol) of (R)-(–)-7,7'-bis(trifluoromethanesulfonyloxy)-2,2'-dimethoxy-1,1'-binaphthyl, 166 mg (0.74 mmol) of $Pd(OAc)_2$, 310 mg (0.75 mmol) of 1,3-diphenylphosphinopropane, 3.4 ml (19.5 mmol) of diisopropylethylamine, and 10 ml (247 mmol) of methanol, and 15 ml of dimethyl sulfoxide and 15 ml of toluene were added thereto. The reaction mixture was heated at 80° C. in a carbon monoxide atmosphere (4 atm) for 65 hours while stirring.

The reaction mixture was cooled to room temperature, water was added, and the mixture was extracted with ethyl acetate. The organic layer was washed successively with a 1N hydrochloric acid aqueous solution, a saturated sodium hydrogencarbonate aqueous solution, and a saturated sodium chloride aqueous solution. The solvent was evaporated, and the residue was purified by silica gel column chromatography using hexane-methylene chloride as an eluent to provide 1.33 g (63%) of the title compound.

Melting point: 222°–223° C. $[\alpha]_D^{22}$: –11.7° (c=1.05, $CHCl_3$).

$^1$H-NMR (270 MHz, $CDCl_3$) δ: 3.76 (s, 6H), 3.77 (s, 6H), 7.57 (d, J=9.2 Hz, 2H), 7.87–7.92 (m, 6H), 8.04 (d, J=9.2 Hz, 2H)

EXAMPLE 5

Synthesis of (R)-(–)-7,7'-Bis(hydroxymethyl)-2,2'-dimethoxy-1,1'-binaphthyl

A mixture of 2.39 g (5.55 mmol) of (R)-(–)-dimethyl 2,2'-dimethoxy-1,1'-binaphthalene-7,7'-dicarboxylate, 1.27 g (33.4 mmol) of lithium aluminum hydride, and 80 ml of THF was stirred under reflux for 33 hours, followed by cooling on an ice bath. To the reaction mixture was slowly added dropwise 1.3 ml of water, 1.3 ml of a 3N sodium hydroxide aqueous solution, and 3.9 ml of water in this order. The reaction mixture was filtered using Celite, and the filtrate was concentrated to yield 2.04 g (98%) of the title compound.

Melting point: 207°–210° C. $[\alpha]_D^{22}$: +46.2° (c=0.53, acetone).

$^1$H-NMR (270 MHz, $CDCl_3$) δ: 3.76 (s, 6H), 4.54 (s, 4H), 7.01 (s, 2H), 7.35 (d, J=8.6 Hz, 2H), 7.45 (d, J=9.2 Hz, 2H), 7.87 (d, J=8.6 Hz, 2H), 7.97 (d, J=9.2 Hz, 2H)

EXAMPLE 6

Synthesis of (R)-7,7'-Bis(bromomethyl)-2,2'-dimethoxy-1,1'-binaphthyl

Triphenylphosphine (4.64 g, 17.7 mmol) was added to a mixture of 2.20 g (5.88 mmol) of (R)-(–)-7,7'-bis(hydroxymethyl)-2,2'-dimethoxy-1,1'-binaphthyl, 4.95 g (14.9 mmol) of carbon tetrabromide, 40 ml of THF, and 10 ml of methylene chloride, followed by stirring at room temperature for 6 hours. The reaction mixture was concentrated, and the residue was purified by silica gel column chromatography (hexane-methylene chloride) to give 2.26 g (77%) of the title compound.

$^1$H-NMR (270 MHz, $CDCl_3$) δ: 3.76 (s, 6H), 4.40 (s, 4H), 7.07 (d, J=2.0 Hz, 2H), 7.37 (dd, J=8.6, 2.0 Hz, 2H), 7.46 (d, J=8.9 Hz, 2H), 7.87 (d, J=8.6 Hz, 2H), 7.97 (d, J=8.9 Hz, 2H)

EXAMPLE 7

Synthesis of (R)-7,7'-Bis(diphenylphosphinomethyl)-2,2'-dimethoxy-1,1'-binaphthyl A solution of 2.60 g (9.93 mmol) of triphenylphosphine and 364 mg (52.4 gram-atom) of lithium in 8.0 ml of THF was stirred at room temperature for 13 hours. To the mixture was added 1.08 ml (9.93 mmol) of 2-chloro-2-methylpropane, followed by further stirring at room temperature for 3 hours. The reaction solution was poured into a mixture of 2.60 g (9.93 mmol) of (R)-7,7'-bis(bromomethyl)-2,2'-dimethoxy-1,1'-binaphthyl and 20 ml of THF, and the mixture was refluxed for 51 hours.

The reaction mixture was cooled to room temperature, and the solvent was evaporated. The residue was dissolved in toluene and washed with water. The solvent was evaporated, and the residue was recrystallized from toluene-ethanol to give 2.11 g (68%) of the title compound.

Melting Point: 146°–148° C. $[\alpha]_D^{26}$: 206.2° (c=1.02, $CHCl_3$).

$^1$H-NMR (270 MHz, $CDCl_3$) δ: 3.31 (d, J=2.3 Hz, 4H), 3.62 (s, 6H), 6.76 (s, 2H), 7.01–7.33 (m, 24H), 7.72 (d, J=8.3 Hz, 2H), 7.87 (d, J=8.9 Hz, 2H).

$^{31}$P-NMR (109 MHz, $CDCl_3$) δ: –10.63 (s).

Elementary Analysis for ($C_{48}H_{40}O_2P_2$): Calcd. (%): C, 81.11; H, 5.67. Found (%): C, 81.23; H, 5.83

EXAMPLE 8

Synthesis of Rhodium Complex $Rh(acac)(CO)_2$ (13 mg, 0.05 mmol) and 36 mg (0.05 mmol) of (R)-7,7'-bis(diphenylphosphinomethyl)-2,2'-dimethoxy-1,1'-binaphthyl were stirred in 0.4 ml of deuterated chloroform ($CDCl_3$). In this state, $^{31}$P-NMR was determined. As a result, the peaks assigned to Rh(acac), (CO), and (L) were observed.

$^{31}$P-NMR (109 MHz, $CDCl_3$) δ: 25.78 (dd, $J_{P-P}$=333.1, $J_{Rh-P}$=140.4 Hz) and 40.68 (dd, $J_{P-P}$=333.1, $J_{Rh-P}$=142.7 Hz)

EXAMPLE 9

A mixture of 127 mg (1.0 mmol) of ethyl 2-cyanopropanoate, 0.12 ml (1.5 mmol) of methyl vinyl ketone, and 9.4 mg (0.01 mmol) of Rh(acac)(CO)(L) obtained in Example 8 was stirred in 5 ml of toluene at 0° C. for 13 hours. The reaction mixture was concentrated to yield 170 mg (86%) of ethyl 5-oxo-2-cyano-2-methylhexanoate. The product was found to have an optical purity of 73% e.e. as analyzed by high performance liquid chromatography using a Chiralcel OJ column manufactured by Daicel Chemical Industries, Ltd.

EXAMPLES 10 TO 12

Isopropyl 5-oxo-2-cyano-2-methylhexanoate and t-butyl 5-oxo-2-cyano-2-methylhexanoate were obtained in the same manner as in Example 9, except for replacing ethyl 2-cyanopropanoate with isopropyl 2-cyanopropanoate or t-butyl 2-cyanopropanoate. The reaction conditions and results obtained are shown in Tables 1 and 2 below.

TABLE 1

| Example No. | Formulae (A) and (B) | | | | Temp. (°C.) | Time (hr) |
|---|---|---|---|---|---|---|
| | $R^1$ | $R^2$ | $R^3$ | Solvent | | |
| 10 | i-Pr | Me | Me | toluene | 30 | 3 |
| 11 | i-Pr | Me | Me | benzene | 0 | 6 |
| 12 | t-Bu | Ne | Me | toluene | 0 | 11 |

TABLE 2

| Example No. | Yield (%) | Optical Purity (% e. e.) | Absolute Configuration |
|---|---|---|---|
| 10 | 90 | 68 | R |
| 11 | 93 | 72 | R |
| 12 | 95 | 66 | R |

While the invention has been described in detail and with reference to specific examples thereof, it will be apparent to one skilled in the art that various changes and modifications can be made therein without departing from the spirit and scope thereof.

What is claimed is:

1. An optically active diphosphine represented by formula:

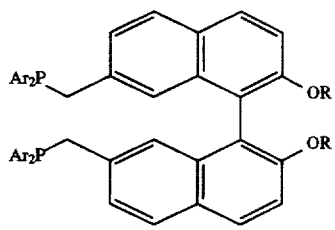

wherein R represents a lower alkyl group having 1 to 4 carbon atoms; Ar represents a phenyl group which may be substituted with a lower alkyl group having 1 to 4 carbon atoms and/or a lower alkoxy group having 1 to 4 carbon atoms.

2. A transition metal complex obtained by reacting a diphosphine represented by formula:

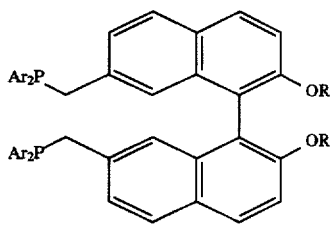

wherein R represents a lower alkyl group having 1 to 4 carbon atoms; Ar represents a phenyl group which may be substituted with a lower alkyl group having 1 to 4 carbon atoms and/or a lower alkoxy group having 1 to 4 carbon atoms, and a transition metal compound.

3. A transition metal complex according to claim 2, wherein said transition metal is selected from the group consisting of ruthenium, rhodium, iridium and palladium.

4. A process for producing an optically active δ-oxo-α-cyano ester represented by formula:

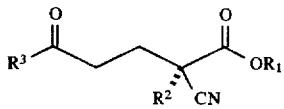

wherein $R^1$ represents an alkyl group having 1 to 8 carbon atoms; $R^2$ represents a lower alkyl group having 1 to 4 carbon atoms; and $R^3$ represents a lower alkyl group having 1 to 4 carbon atoms or a substituted or unsubstituted phenyl group, comprising adding an α-cyano ester represented by formula:

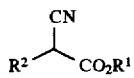

to a vinyl ketone compound represented by formula:

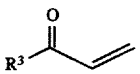

in the presence of a transition metal complex obtained by reacting a diphosphine represented by formula:

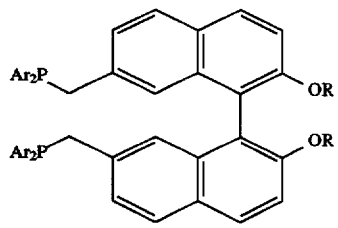

wherein R represents a lower alkyl group having 1 to 4 carbon atoms; Ar represents a phenyl group which may be substituted with a lower alkyl group having 1 to 4 carbon atoms and/or a lower alkoxy group having 1 to 4 carbon atoms, and a transition metal compound.

* * * * *